United States Patent [19]

Brake

[11] Patent Number: 4,595,785

[45] Date of Patent: Jun. 17, 1986

[54] PREPARATION OF DIMETHYL ETHER BY CATALYTIC DEHYDRATION OF METHANOL

[75] Inventor: Loren D. Brake, Wilmington, Del.

[73] Assignee: E. I. DuPont de Nemours and Company, Wilmington, Del.

[21] Appl. No.: 707,606

[22] Filed: Mar. 4, 1985

Related U.S. Application Data

[63] Continuation-in-part of Ser. No. 505,356, Jun. 16, 1983, abandoned.

[51] Int. Cl.$^4$ ............................................. C07C 41/09
[52] U.S. Cl. ................................................. 568/698
[58] Field of Search ........................................ 568/698

[56] References Cited

U.S. PATENT DOCUMENTS 1,873,537  8/1932  Brown et al.
2,014,408  9/1935  Woodhouse.

FOREIGN PATENT DOCUMENTS 403402  11/1933  United Kingdom.

OTHER PUBLICATIONS

Mantell, Adsorption, Chemical Engineering Series, McGraw Hill Book Co., New York, 1951, pp. 89-91.

*Primary Examiner*—Howard T. Mars

[57] ABSTRACT

In the preparation of dimethyl ether by the catalytic dehydration of methanol, reaction rate is enhanced and catalyst coking and byproduct formation are significantly reduced when an aluminotitanate containing 0.1-20% of titania and 80-99.9% of alumina is used as the catalyst.

3 Claims, No Drawings

PREPARATION OF DIMETHYL ETHER BY CATALYTIC DEHYDRATION OF METHANOL

CROSS-REFERENCE TO RELATED APPLICATIONS

This application is a continuation-in-part of application Ser. No. 505,356, filed June 16, 1983 now abandoned.

DESCRIPTION

Technical Field

This invention relates to an improved method for the preparation of dimethyl ether by the catalytic dehydration of methanol. It is more particularly directed to such a method in which the catalyst used is an aluminotitanate.

Background and Summary of the Invention

Dimethyl ether is a commodity in the chemical industry, widely used as a starting material in the preparation of other chemicals such as dimethyl sulfate, and more recently as a propellant in aerosol containers.

One of the commonly used methods for preparing dimethyl ether is the catalytic dehydration of methanol, using a phosphoric acid-alumina catalyst. While that process is generally satisfactory, the catalyst has a tendency to coke, which requires it to be replaced more frequently than is desirable. By "coke" is meant the phenomenon by which the surface of the catalyst becomes coated with carbon, thus blocking its pores and reducing its effectiveness.

It has now been found that this coking can be minimized if, instead of the phosphoric acid-alumina catalyst, one uses an aluminotitanate catalyst containing 0.1–20% by weight of titania and 80–99.9% by weight of gamma-alumina. Surprisingly, use of such a catalyst not only reduces the amount of coking but also significantly increases the rate of the dehyration reaction over that obtained with the phosphoric acid-alumina catalyst, and greatly reduces the number and amounts of byproducts formed, notably hydrogen, carbon monoxide, methane, ethane, propane, ethylene, propylene and various ethers having high boiling points.

DETAILED DESCRIPTION OF THE INVENTION

The catalytic dehydration of methanol to form dimethyl ether is well known and is described in detail in U.S. Pat. No. 2,014,408 to John C. Woodhouse.

The reaction proceeds according to the general equation

$$2CH_3OH \rightleftharpoons CH_3OCH_3 + H_2O$$

The product of the reaction is a mixture principally containing dimethyl ether, unreacted methanol and water.

The reaction is ordinarily conducted continuously in a column reactor, in the vapor phase, generally at a maximum reactor bed temperature of 200°–500° C., preferably 275°–420° C., and a pressure ranging from ambient to 3447 kPa (gauge), preferably 1034–1723 kPa (gauge). The catalyst is packed into the reactor in the customary way, and the vaporized and preheated (200°–300° C.) methanol is passed through it, preferably downwardly.

Residence time of the methanol in the reactor is selected according to well-known chemical engineering principles, as are the methods of recovering the dimethyl ether from the reactor effluent and the methods of refining it.

The catalysts used according to the invention are aluminotitanates containing 0.1–20% by weight of titania and 80–99.9% by weight of gamma alumina, preferably 0.2–10% of titania and 90–99.5% of alumina, even more preferably about 1% of titania and about 99% of alumina.

The catalysts can contain the titania distributed throughout the alumina, i.e., they can be homogeneous catalysts, or they can contain the titania as a coating on the alumina.

The homogeneous catalysts can be made by mixing aqueous solutions of $TiCl_4$ and sodium aluminate, in proportions precalculated to give the desired titania/alumina ratio, and then bringing the solution to a pH of about 8 with hydrochloric acid, at a temperature of 50°–70° C. The resulting gel, a mixture of hydroxides, is recovered, washed free of chlorides with water, dried to a free-flowing powder, shaped and then calcined at 450°–650° C. to give a material which can be used directly as the catalyst.

The catalyst of alumina coated with titania can be made by first preparing a pourable aqueous slurry of boehmite or gamma alumina powder and then adding to it, with vigorous stirring, an aqueous 10–20% by weight solution of $TiCl_4$, in proportions precalculated to give the desired alumina-titania ratio. The slurry is then adjusted to a pH of about 8 with NaOH and is held for 30 minutes, with stirring, at 50°–70° C. The solids are then removed by filtration or centrifugation, dried to a free-flowing powder, shaped and then calcined at 500°–550° C.

The catalyst is generally used as shaped forms, ordinarily pellets or spheroids. Form size is selected according to recognized chemical engineering principles, and is usually in the range 2–120 mm in all dimensions. The pore volume, pore size and total surface area of the forms are likewise a matter of choice, and will generally be in the range of 0.2–0.8 cc/g, greater than 25 angstrom units, and 100–250 m$^2$/g, respectively.

EXAMPLE

In the following example, all parts are by weight.

Forty-five parts of an homogeneous aluminotitanate containing about 99% of gamma alumina and about 1% of titania, in the form of spheroids having diameters of 3.15 mm, were mixed with 319 parts of glass spheroids having diameters of 4 mm.

The mixture was packed into a column reactor having a length/diameter ratio of 4.

Methanol, preheated to 300° C., was then continuously fed into the top of the reactor. The vapors were passed downwardly through the catalyst bed at the rate of 660 parts per hour. Pressure in the reactor was held at 1034 kPa (gauge); the reactor bed temperature reached a maximum of 400° C.

The vapors leaving the reactor were condensed to give a product having the average composition
Dimethyl ether: 57.5%
Methanol: 20%
Water: 22.5%

I claim:

1. In the preparation of dimethyl ether by the catalytic dehydration of methanol, the improvement which comprises using as the catalyst an aluminotitanate which contains, by weight, 0.1–20% of titania and 80–99.9% of alumina.

2. The process of claim 1 in which the catalyst contains 0.2–10% of titania and 90–99.5% of alumina.

3. The process of claim 1 in which the catalyst contains about 1% of titania and about 99% of alumina.

* * * * *